United States Patent [19]
Adahan

[11] Patent Number: 5,381,829
[45] Date of Patent: Jan. 17, 1995

[54] FLUID MIXING DEVICE AND DEMAND VALVE USEFUL THEREWITH

[76] Inventor: Carmeli Adahan, Netivei Am 11, Ramot Gimmel, 97552 Jerusalem, Israel

[21] Appl. No.: 116,173

[22] Filed: Sep. 2, 1993

Related U.S. Application Data

[63] Continuation of Ser. No. 926,623, Aug. 10, 1992, abandoned.

[51] Int. Cl.6 .............................................. F16K 11/02
[52] U.S. Cl. ............................ 137/625.17; 137/505.25
[58] Field of Search ..................... 137/625.17, 505.25

[56] References Cited

U.S. PATENT DOCUMENTS

| | | | |
|---|---|---|---|
| 3,347,268 | 10/1967 | Muller | 137/625.17 |
| 3,358,714 | 12/1967 | Moen | 137/625.17 |
| 3,416,570 | 12/1968 | Kervin | 137/625.17 |
| 3,890,999 | 6/1975 | Moskow | 137/505.25 |
| 4,015,630 | 4/1977 | Contreras | 137/505.25 |
| 4,083,380 | 4/1978 | Huber | 137/595.25 |
| 4,436,090 | 3/1984 | Darling | |
| 4,702,240 | 10/1987 | Chaoui | |
| 4,765,356 | 8/1988 | Hallberg | 137/625.17 X |
| 5,095,950 | 3/1992 | Hallberg | |

*Primary Examiner*—Stephen M. Hepperle
*Attorney, Agent, or Firm*—Benjamin J. Barish

[57] ABSTRACT

A fluid mixing device includes a housing having two inlets for two fluids to be mixed, a common outlet, and a cylindrical chamber connecting the inlets to the outlet. A valve member is disposed within the cylindrical chamber and includes a cylindrical wall formed with a slot extending for a part of the wall circumference. The housing inlets include slots extending transversely of the cylindrical chamber. The valve member is displaceable axially for moving its slot into or out of alignment with the inlet slots. It is also presettable angularly to permit presetting the proportion the valve member slot is coextensive with the inlet slots, and thereby the proportions of the inletted fluids to be included in the outlet mixture. Also described is a demand valve optionally usable with the fluid mixing device.

16 Claims, 1 Drawing Sheet

FLUID MIXING DEVICE AND DEMAND VALVE USEFUL THEREWITH

This application is a continuation, of application Ser. No. 07/926,623 filed Aug. 10, 1992, now abandoned.

FIELD AND BACKGROUND OF THE INVENTION

The present invention relates to fluid mixing devices and to demand valves useful with such devices. The invention is particularly useful for blending air and oxygen in order to obtain a mixture having a preselected percentage of oxygen (e.g., for administering to respiratory patients), and is therefore described below with respect to such an application.

At the present time, various types of fluid mixing devices are commercially available for mixing air and oxygen. According to one known method, air and oxygen are inletted via orifices whose cross-sectional area can be preset, as by a control knob, in order to obtain any desired mixture ratio. In another known method, a predetermined quantity of oxygen is introduced into a reservoir, and then ambient air is drawn in to produce the desired mixture. According to a third known method, oxygen is caused to flow at a high rate through a venturi to produce a low pressure which draws air through a nozzle, the air/oxygen ratio being controlled by the opening size of the nozzle.

The above known systems are generally not accurate in delivering a fixed ratio of air/oxygen under a wide variation of flow rates, and/or require extremely accurate hardware to perform the mixing since they depend on size and shape of orifices in a valve or nozzle for this purpose. Some constructions provide accuracy at high flow rates but not at low flow rates, whereas other constructions have high flow resistance at high flow rates, and poor ratio control at low flow rates.

It would therefore be desirable to provide a fluid mixing device of a simple construction which can provide relatively accurate ratio control particularly at a wide range of flow rates.

BRIEF SUMMARY OF THE INVENTION

According to the present invention, there is provided a fluid mixing device, comprising a housing having a plurality of inlets for a plurality of fluids to be mixed, an outlet for the mixed fluids, and a cylindrical chamber connecting the inlets to the outlet; an opening from each of the inlets to the cylindrical chamber; and a valve member axially and rotatably displaceable within the cylindrical chamber. The valve member includes a cylindrical wall having one end open and communicating with the outlet, and an opposite end closed by an end wall facing a portion of the housing. The cylindrical wall of the valve member is formed with slot means alignable with the plurality of inlets for presetting the ratio of inletted fluids to be outletted according to the rotated position of the valve member. The fluid mixing device further includes a spring biasing the valve member to a closed position wherein the end wall is moved towards the portion of the housing which it faces, and the slot means is moved out of alignment with the plurality of inlets; and a vent opening to a constant reference pressure through the portion of the housing faced by the end wall of the valve member. The arrangement is such that the valve member is effective to open and close all the inlets the same amount according to the pressure at the outlet alone and independently of the pressure at any of the inlets.

A fluid mixing device constructed in accordance with the foregoing features is particularly useful as a relatively inexpensive flow proportioner for mixing air and oxygen (or other fluids) according to a preselected ratio and for maintaining such a ratio at different output flow rates. Thus, the ratio can be preselected as desired from 100% of one fluid (e.g., air) to 100% of the other fluid (e.g., oxygen), and maintained substantially constant under different output flow rates.

According to further features in the described preferred embodiment, the fluid mixing device may be used in combination with a demand valve for reducing the pressure of one of the fluids applied to the inlet of the fluid mixing device, e.g., the oxygen inlet, the demand valve including a housing removably attached to the respective inlet of the fluid mixing device.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
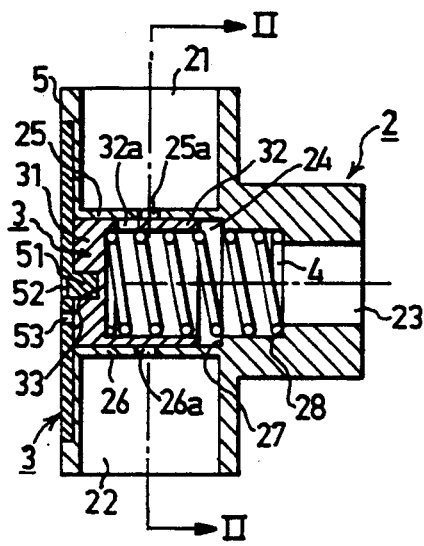
FIG. 1 is a longitudinal sectional view illustrating one form of fluid mixing device constructed in accordance with the present invention.
Figure 2:
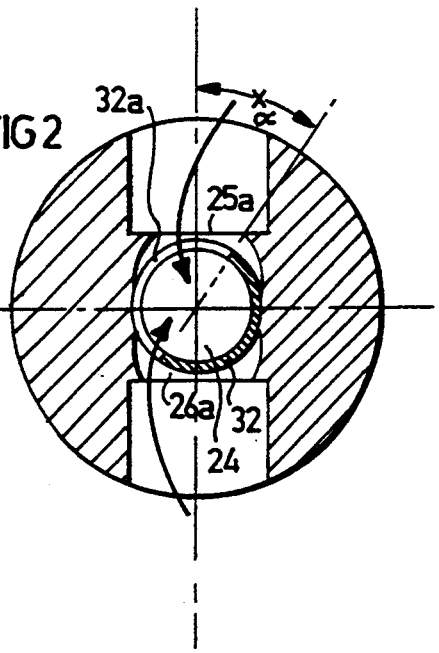
FIG. 2 is a sectional view, along line II—II of FIG. 1 in the operative condition of the device.

The fluid mixing device illustrated in FIGS. 1 and 2 of the drawings is particularly useful for producing a mixture of air and oxygen at a preselected ratio e.g., for administering to respiratory patients. The illustrated device is of a simple construction, including but four main parts, namely: a housing 2, a valve member 3, a spring 4 and a cover plate 5, which is actually a part of housing 2.

The housing 2 is formed with a first inlet 21 (e.g., for the oxygen), a second inlet 22 (e.g., for the air), and an outlet 23 for outletting the mixture of air and oxygen. Housing 2 is further formed with a cylindrical chamber 24 connecting the two inlets 21, 22 with the outlet 23. As clearly seen in FIG. 1, the two inlets 21, 22 are diammetrically opposed with respect to each other on opposite sides of housing 2 and extend in the radial direction with respect to the cylindrical chamber 24; whereas the outlet 23 is coaxial with the cylindrical chamber.

Housing inlet 21 includes an end wall 25 formed with an elongated slot 25a extending transversely of, and communicating with, chamber 24. Housing inlet 22 includes a similar end wall 26 formed with a similar slot 26a extending transversely of, and communicating with, the chamber. As shown in FIG. 2, the two slots 25a, 26a are aligned with each other.

Housing 2 is further formed with a first annular shoulder 27 and a second annular shoulder 28, both coaxial with respect to the housing outlet 23.

Valve member 3 is disposed within the cylindrical chamber 24. The valve member includes an end wall 31 engageable with the housing cover plate 5, and a cylindrical wall 32 having an outer diameter slidably fitted to the diameter of the cylindrical chamber 24, so that the valve member is angularly displaceable within the cylindrical chamber. In addition, the length of valve member 3 (i.e., the distance between the outer face of its end wall 31 and the opposite end of its cylindrical wall 32) is less than the distance between the inner face of cover plate 5 and annular shoulder 27, so that the valve member is also displaceable axially within the cylindrical chamber 24.

Cylindrical wall 32 of the valve member is formed with a slot 32a extending circumferentially for about one-half of its circumference as shown in FIG. 2. Coiled spring 4 is interposed between the inner face of end wall 31 of the valve member and annular shoulder 28 of the housing, and biases the valve member to a normal position against cover plate 5. In this normal position, slot 32a of the valve member is out of alignment with both of the slots 25a, 26a, in the two inlet walls 25, 26. However, the valve member 3 is displaceable axially to bring its slot 32a into alignment with the two inlet slots 25a, 26a during the normal operation of the device, as will be described more particularly below.

The angular displacement of valve member 3 is effected by rotating the cover plate 5. For this purpose, the cover plate 5 is coupled to valve member 3 by a key 51 projecting from a rear surface of the housing cover plate received within a slot 33 in the valve end wall 31. Cover plate 5 may be rotated in any convenient manner, e.g., by the provision of a screwdriver slot 52 on its front face, by a knob (not shown), etc. Cover plate 5 is further formed with a vent or opening 53 for venting to a constant reference pressures, viz the atmosphere, the space between its inner face and the outer face of the valve member end wall 31.

The fluid mixing device illustrated in FIGS. 1 and 2 is used in the following manner:

The mixing ratio of the two fluids (e.g., oxygen and air) inputted via the inlets 21, 22 is first preset by rotating the cover plate 5, which in turn rotates valve member 3 and its cylindrical wall 32. This presets the proportion slot 32a of the valve cylindrical wall 32 to become aligned with each of the two slots 25a, 26a in the inlet end wall 25, 26, respectively. Thus, as shown in FIG. 2, the angle $\alpha$ to which valve member 3 is rotated will determine the oxygen/air ratio of the mixture outletted via outlet 23. FIG. 2 illustrates a presetting wherein a substantially larger portion of the valve member slot 32a is in alignment with the oxygen inlet slot 25a so that most of the outletted mixture will be oxygen. Clockwise rotation of valve member 3 will increase the proportion of oxygen in the outletted mixture, whereas counter-clockwise rotation of the valve member will decrease the proportion of the oxygen in the outletted mixture.

After the device has been thus preset, the preset ratio will be maintained relatively constant during various output flow rates. Coil spring 4 normally biases valve member 3 against the cover plate 5, with the valve member slot 32a out of alignment with both the inlet slots 25a, 26a, so that no fluid will be outletted to the outlet chamber 23. Vent opening 53 in cover plate 5 assures that ambient pressure will always be maintained in the space between valve end wall 31 and the cover plate 5.

Accordingly, the valve member will move axially within chamber 25 in response to the negative pressure (vacuum) applied to its outlet 23 from the device (e.g., a respiratory device), to which the air/oxygen mixture is to be supplied. Thus, when the air/oxygen mixture is to be supplied, the respiratory device applies a negative pressure to outlet chamber 23 sufficient to overcome spring 4 and to move valve member 3 axially so as to bring its slot 32a into alignment with the two slots 25a, 26a. The preset angular position of valve member 3 will determine the ratio of oxygen/air to be supplied from the two inlets 21, 22, respectively, as described above. This ratio will be maintained for all changes in the overall flow rate since key 51, received within slot 33 of the end wall 31, prevents any angular displacement of the valve member during its axial displacement in response to flow rate change.

If a higher outflow of the oxygen/air mixture is required, the vacuum (negative pressure) at outlet 23 will be increased, thereby moving valve member 3 axially to bring a larger portion of its slot 32a into alignment with the two slots 25a, 26a until limited by the engagement of the open end of the valve member cylinder 32 with the annular shoulder 27; and if a smaller outflow is required, the vacuum at outlet 23 will be decreased, whereby spring 4 moves the valve member 3 to bring a smaller portion of its slot 32a into alignment with the two inlet slots 25a, 26a. However, in any axial position of the valve member 3, its angular position remains substantially the same by key 51 movable within slot 33. Thus, the two inlet slots 25a and 26a are opened or closed by the interconnecting slot 32a simultaneously, and in the same proportion, so that the output ratio of the two gasses (determined by the angular position of the valve member) remains substantially constant with all output flow rates (determined by the axial position of the valve member).

It will thus be seen that the described device can mix gasses or other fluids at ambient pressure or at high pressure. For example, a demand valve or pressure regulator can be used to reduce a high pressure to ambient pressure at one or both gas inlets.

Figure 3:
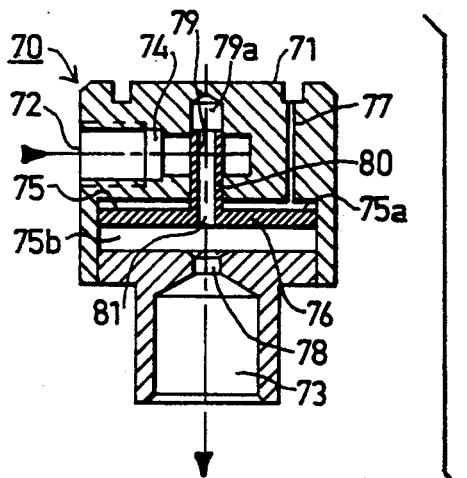
FIG. 3 illustrates an assembly including the fluid mixing device of FIGS. 1 and 2 in combination with a demand valve.
Figure 3:
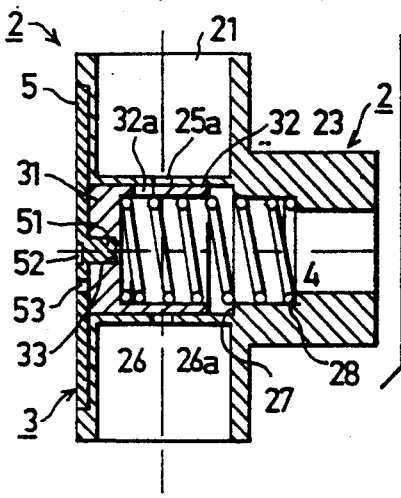

FIG. 3 illustrates an assembly including a combination of the fluid mixing device of FIGS. 1 and 2, therein generally designated 2, and a demand valve, therein generally designated 70. The fluid mixing device 2 illustrated in FIG. 3 is of the same construction as described above with respect to FIGS. 1 and 2, and therefore corresponding parts have been correspondingly numbered to facilitate understanding.

The demand valve 70 is attachable to the oxygen inlet 21 of the fluid mixing device 2 in order to supply the oxygen thereto whenever demanded, as manifested by a reduction in pressure at the outlet 23. The demand valve also reduces the pressure to that of the air supplied via the inlet 22, which is generally at ambient pressure. Such a demand valve is particularly useful where the oxygen is supplied from a high pressure source (e.g., 50 psi), whereas the air is supplied at ambient pressure.

The demand valve 70 includes a housing 71 having an inlet 72 connectible, as by threads, to the high pressure source of oxygen, and an outlet 73 connectible to the oxygen inlet 21 of the fluid mixing device 2. A filter 74 is inserted in inlet 72 to exclude contaminants from the supplied oxygen.

Housing 71 is further formed with a compartment 75 between the inlet 72 and outlet 73. A piston 76 is disposed within compartment 75 and divides it into an inlet control chamber 75a on one side of the piston, and an outlet control chamber 75b on the opposite side of the piston. Inlet control chamber 75a is vented to the atmosphere via a vent 77. Outlet control chamber 75b communicates with the outlet 73 via an orifice 78.

Housing 71 is further formed with a bore 79 connecting the inlet 72 to the internal compartment 75. Bore 79 extends perpendicularly to the inlet 72 and extends into the housing wall at the inlet so as to provide a recess 79a in the housing wall. Piston 76 includes a stem 80 which is formed with a hollow passageway 81 extending through the stem and also through the piston.

The demand valve 70 illustrated in FIG. 3 operates as follows:

When the fluid mixing device 2 is to be supplied with pressurized gas (e.g., oxygen), the outlet 73 of the demand valve 70 is attached, e.g., by a force-fit, to the inlet 21 of the mixing device 2. If there is no flow through the outlet 23 of the mixing device, any leakage at the inlet 21 will build up a pressure in the outlet control chamber 75b. Accordingly, the piston 76 will normally be in its upper position, with the upper end of its stem 80 received within recess 79a of the demand valve housing 70. If, however, the piston 76 is in a lower position, as soon as pressurized oxygen flows into the demand valve inlet 72, it will pressurize the outlet control chamber 75b, and therefore the piston will then move up to its closed condition with the upper end of its stem 80 received within recess 79a.

Whenever oxygen is demanded, a vacuum is produced in the outlet control chamber 75b via the outlet 23 of the mixing device 2. This vacuum draws piston 76 downwardly, to cause its stem 80 to move out of recess 79a, thereby establishing communication between the inlet 72 and the outlet 73 of the demand valve 70.

Piston 76 will thereafter float towards and away from orifice 78 to regulate the pressure in outlet control chamber 75b. Thus, if the flow rises, the pressure within chamber 75b will decrease, thereby moving piston 76 closer to orifice 78 to increase the opening between inlet 72 and bore 79; and if the flow drops, the pressure within chamber 75b will increase, thereby moving the piston 76 away from orifice 78 to decrease the opening between inlet 72 and bore 79.

Figure 4:
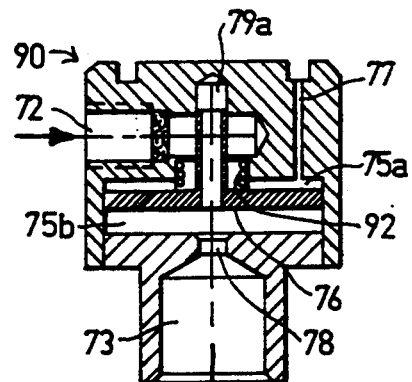
FIG. 4 illustrates a modification in the construction of the demand valve of FIG. 3.

FIG. 4 illustrates a demand valve, therein designated 90, which is of identical construction as demand valve 70 in FIG. 3, and therefore its corresponding parts are correspondingly numbered, except that the demand valve 90 in FIG. 4 includes a control spring 92 urging the piston 76 towards the orifice 78. The addition of the control spring 92 requires a higher pressure in the control chamber 75b to balance the forces on both sides of the piston. Thus, the pressure in chamber 75b will be regulated to a higher level than ambient, as controlled by the force of spring 92. Spring 92 thus converts the demand valve to a pressure regulator.

While the invention has been described with respect to one preferred embodiment, it will be appreciated that many other variations, modifications and applications of the invention may be made.

What is claimed is:

1. A fluid mixing device, comprising:
a housing having a plurality of inlets for a plurality of fluids to be mixed, an outlet for the mixed fluids, and a cylindrical chamber connecting said inlets to said outlet;
an opening from each of said inlets to said cylindrical chamber;
a valve member axially and rotatably displaceable within said cylindrical chamber;
said valve member including a cylindrical wall having one end open and communicating with said outlet, and an opposite end closed by an end wall facing a portion of said housing;
said cylindrical wall of the valve member being formed with slot means alignable with said plurality of inlets for presetting the ratio of inletted fluids to be outletted according to the rotated position of the valve member;
a spring disposed between said valve end wall and said housing and biasing said valve member to a closed position wherein said end wall is moved towards said portion of the housing which it faces, and said slot means is moved out of alignment with said plurality of inlets;
and a vent opening through said portion of the housing to a constant reference pressure;
said valve member being movable axially within said cylinder chamber automatically in response to the difference between said reference pressure and said outlet pressure whereby the valve member is effective to open and close all said inlets the same amount according to the pressure at said outlet alone and independently of the pressure at any of said inlets.

2. The fluid mixing device according to claim 1, wherein said housing is formed with an annular shoulder between said cylindrical chamber and said outlet, said spring being disposed within said cylindrical wall with one end seated in said annular shoulder, and the opposite end bearing against said end wall of the valve member and urging said end wall towards said portion of the housing it faces.

3. The fluid mixing device according to claim 2, wherein said inlet openings are elongated slots extending transversely of said chamber, and said slot means in the cylindrical wall of the valve member includes a slot extending circumferentially of the valve member.

4. The fluid mixing device according to claim 3, wherein said elongated slot extends for about one-half the circumference of the valve member cylindrical wall.

5. The fluid mixing device according to claim 4, wherein said cylindrical wall includes a second annular shoulder between said cylindrical chamber and said outlet, said spring urging the valve member to its closed position wherein the open end of the cylindrical wall is spaced away from said second annular shoulder but permits the valve member to move to an open position until limited by said second annular shoulder.

6. The fluid mixing device according to claim 1, wherein said housing includes two inlets on diametrically opposite sides of said chamber, and said housing outlet is coaxial with said chamber.

7. A fluid mixing device, comprising:
a housing having a plurality of inlets for a plurality of fluids to be mixed, an outlet for the mixed fluids, and a cylindrical chamber connecting said inlets to said outlet;
an opening from each of said inlets to said cylindrical chamber;
a valve member axially and rotatably displaceable within said cylindrical chamber;

said valve member including a cylindrical wall having one end open and communicating with said outlet, and an opposite end closed by an end wall facing a portion of said housing;

said cylindrical wall of the valve member being formed with slot means alignable with said plurality of inlets for presetting the ratio of inletted fluids to be outletted according to the rotated position of the valve member;

a spring biasing said valve member to a closed position wherein said end wall is moved towards said portion of the housing which it faces, and said slot means is moved out of alignment with said plurality of inlets;

and a vent opening through said portion of the housing a constant reference pressure;

said valve member being movable axially within said cylinder chamber automatically in response to the difference between said reference pressure and said outlet pressure whereby the valve member is effective to open and close all said inlets the same amount according to the pressure at said outlet alone and independently of the pressure at any of said inlets, wherein said portion of the housing faced by said end wall is a rotatable cover plate coupled to said valve member to displace it angularly when the cover plate is rotated.

8. The fluid mixing device according to claim 7, wherein said cover plate is coupled to said valve member by a key formed in the cover plate received in a recess formed in said valve member.

9. A fluid mixing device, comprising:

a housing having a pair of inlets on diametrically opposite sides thereof for inletting two fluids to be mixed, and a cylindrical chamber connecting said inlets to an outlet coaxial with said chamber;

a valve member within said chamber and including a cylindrical wall formed with a slot extending circumferentially for about one-half of its circumference, one end of said cylindrical wall being open and communicating with said outlet, the opposite end of said cylindrical wall being closed by an end wall facing a portion of said housing;

said housing inlets including slots aligned with each other and extending tranversely of said cylindrical chamber;

said valve member being presettable angularly within said chamber to permit presetting the proportion its slot is coextensive with the respective inlet slots when aligned therewith, and thereby the proportion of each of the inletted fluids in the outletted mixture;

a spring disposed between said valve end wall and said housing and biasing said valve member to a closed position wherein said end wall is moved towards said portion of the housing which it faces, and said slot means is moved out of alignment with said plurality of inlets;

and a vent opening through said portion of the housing to a constant reference pressure;

said valve member being movable axially within said cylinder chamber automatically in response to the difference between said reference pressure and said outlet pressure whereby the valve member is effective to open and close all said inlets the same amount according to the pressure at said outlet alone and independently of the pressure at any of said inlets.

10. The fluid mixing device according to claim 9, wherein said housing is formed with an annular shoulder between said cylindrical chamber and said outlet, said spring being disposed within said cylindrical wall with one end seated in said annular shoulder, and the opposite end bearing against said end wall of the valve member and urging said end wall towards said portion of the housing it faces.

11. The fluid mixing device according to claim 9, wherein said portion of the housing faced by said end wall is a rotatable cover plate coupled to said valve member to displace it angularly when the cover plate is rotated, said cover plate being coupled to said valve member by a key formed in the cover plate received in a recess formed in said valve member.

12. The combination of a fluid mixing device according to claim 1, and a demand valve for reducing the pressure of one of the fluids applied to the respective inlet of the fluid mixing device, said demand valve including a housing removably attached to the respective inlets of the fluid mixing device.

13. The combination according to claim 12, wherein:

said demand valve housing includes an inlet, an outlet, a compartment connecting the inlet to the outlet, a piston in said compartment to define an inlet control chamber on one side of the piston and an outlet control chamber on the opposite side of the piston, and a vent venting the inlet control chamber to the atmosphere;

said piston being displaceable within said compartment towards and away from said outlet to control the flow therethrough in response to the vacuum in said control chamber.

14. The combination according to claim 13, wherein said demand valve further includes a spring normally biassing said piston towards said outlet orifice.

15. The combination according to claim 13, wherein said piston includes a stem having its outer end receivable in a bore communicating with the demand valve inlet and terminating in a recess in said housing, said stem including a passageway extending therethrough and through said piston and being displaceable with the piston from a closed position with its outer end received within said recess to block the flow of fluid from said demand valve inlet to said outlet control chamber, to an open position with its outer end spaced from said recess to open the flow of fluid from said demand valve inlet to said outlet control chamber.

16. The combination according to claim 15, wherein said demand valve further includes a spring normally biassing said piston towards said outlet orifice and said stem away from said recess.

* * * * *